US010913058B2

(12) United States Patent
Ohba et al.

(10) Patent No.: US 10,913,058 B2
(45) Date of Patent: Feb. 9, 2021

(54) PURIFICATION PROCESS FOR HYDROLYSABLE ORGANIC SOLVENT

(71) Applicant: Dow Global Technologies LLC, Midland, MI (US)

(72) Inventors: Kaoru Ohba, Tokyo (JP); Kenji Takano, Niigata (JP); Masonori Iida, Tokyo (JP); Shinnosuke Abe, Tokyo (JP); Takashi Masudo, Natori (JP); Osamu Kishizaki, Tokyo (JP); Ryo Ishibashi, Tokyo (JP); Yusuke Yamashita, Tokyo (JP)

(73) Assignee: Dow Global Technologies LLC, Midland, MI (US)

( * ) Notice: Subject to any disclaimer, the term of this patent is extended or adjusted under 35 U.S.C. 154(b) by 23 days.

(21) Appl. No.: 16/067,041

(22) PCT Filed: Dec. 16, 2016

(86) PCT No.: PCT/US2016/067180
§ 371 (c)(1),
(2) Date: Jun. 28, 2018

(87) PCT Pub. No.: WO2017/116759
PCT Pub. Date: Jul. 6, 2017

(65) Prior Publication Data
US 2019/0009267 A1   Jan. 10, 2019

(30) Foreign Application Priority Data
Dec. 28, 2015 (JP) .................................. 2015-256088

(51) Int. Cl.
| C07C 67/56 | (2006.01) |
| B01J 47/04 | (2006.01) |
| B01J 41/07 | (2017.01) |
| B01D 15/00 | (2006.01) |
| B01J 39/05 | (2017.01) |
| B01J 39/07 | (2017.01) |
| B01D 15/36 | (2006.01) |
| B01J 39/18 | (2017.01) |
| B01J 41/12 | (2017.01) |

(52) U.S. Cl.
CPC .............. *B01J 47/04* (2013.01); *B01D 15/00* (2013.01); *B01D 15/362* (2013.01); *B01D 15/363* (2013.01); *B01J 39/05* (2017.01); *B01J 39/07* (2017.01); *B01J 39/18* (2013.01); *B01J 41/07* (2017.01); *B01J 41/12* (2013.01); *C07C 67/56* (2013.01)

(58) Field of Classification Search
None
See application file for complete search history.

(56) References Cited

U.S. PATENT DOCUMENTS

| 5,192,446 A | 3/1993 | Salem et al. |
| 5,518,628 A | 5/1996 | Carey |
| 6,123,850 A | 9/2000 | Commarieu et al. |
| 6,200,479 B1 | 3/2001 | Zampini et al. |
| 7,329,354 B2 | 2/2008 | Mullee |
| 2018/0273465 A1 | 9/2018 | Muneyasu |

FOREIGN PATENT DOCUMENTS

| JP | 10228560 | 9/1989 |
| JP | 2004249238 A | 9/2004 |
| JP | 5096907 B2 | 12/2012 |
| WO | 2003/020393 A1 | 3/2003 |

OTHER PUBLICATIONS

English Translation of Kato et al. (JP 10228560, published 1989).*
Dupont Product Data Sheet for Amberlyst 21.*
Sigma Product Data Sheet for Amberlyst 15.*
PCT/US2016/067180, International Search Report and Written Opinion dated Feb. 21, 2017.
PCT/US2016/067180, International Preliminary Report on Patentability dated Jul. 3, 201.
EP Appln. No. 16882337.5-1104, Extended European Search Report dated Jul. 24, 2019.

* cited by examiner

*Primary Examiner* — Sudhakar Katakam
*Assistant Examiner* — Jennifer C Sawyer

(57) ABSTRACT

Methods for the removal of ionic contaminants from hydrolysable organic solvent by ion exchange resins are described. A mixed bed of ion exchange resin with cationic ion exchange resin and weak-base anionic ion exchange resin is used in such methods.

5 Claims, No Drawings

PURIFICATION PROCESS FOR HYDROLYSABLE ORGANIC SOLVENT

FIELD

The present invention relates generally to methods for removal of contaminants from hydrolysable organic solvent. In particular, the present invention relates to methods for removal of metallic and non-metallic ionic contaminants from hydrolysable organic solvent by ion exchange resin without substantial hydrolysis reaction.

INTRODUCTION

Pure solvent free of ionic contaminants is required for many industrial purposes such as for the manufacture of pharmaceuticals and electronic materials. Especially, organic solvents with a quite low level of metallic ion contaminants are required for semiconductor fabrication processes, because the contamination of metal ions negatively affects the performance of semiconductor devices. Some hydrolysable organic solvents are useful for semiconductor fabrication processes. For example, propylene glycol methyl ether acetate (PGMEA) is commonly used for lithography processes in semiconductor fabrication processes. Therefore, when hydrolysable organic solvents are to be used in semiconductor fabrication processes, it would be desirable for such solvents to have a quite low level of metallic ion contaminants.

Ion exchange resins have been used for purification of water by removing ionic contaminants from water. Recently, such ion exchange technology has been applied in the purification of organic solvents which are used in manufacturing electronic materials. However, it is believed that the behavior of ionic contaminants in organic solvent is different from their behavior in water because of the differences in polarities, such that the technology for purification of water using ion exchange resin is not generally expected to be suitable for use in the purification of organic solvent directly.

Previous methods for metal ion removal from organic solvents have been disclosed. U.S. Pat. No. 7,329,354 discloses a system for purification of an organic solvent by ion exchange resin. JP5,096,907B discloses a method for removal of anionic impurities from an ester by weak anionic exchange resin or anionic exchange resin in which OH groups in the anionic exchange resin are capped and inactivated. U.S. Pat. No. 6,123,850 discloses a method for purification of virtually anhydrous organic liquids by a cationic exchange resin based on a polystyrene-divinylbenzene copolymer with quite high contents (50-60%) of divinylbenzene. U.S. Pat. No. 5,518,628 discloses a method for removal of ionic contamination from an organic solution using a mixed bed of ion exchange resin in which strong-base anionic exchange resin of the mixed bed of ion exchange resin is modified by an ammonium salt of a weak organic acid.

However, these processes are insufficient for the removal of ionic contaminants and/or cause hydrolyzed reactions such that obtained organic solvents are not suitable for applications requiring a quite high level of purity. Therefore, a process for removal of a high level of ionic contaminants from hydrolysable organic solvent is desired.

SUMMARY

The present invention provides a process for removal of ionic contaminants with a quite high-level from hydrolysable organic solvent without hydrolyzed reactions. The process uses mixed bed of ion exchange resins comprising cationic ion exchange resin and weak-base anionic ion exchange resin. In using a weak-base anionic exchange resin in the mixed bed of ion exchange resins, the hydrolyzed reaction of hydrolysable organic solvent can be avoided without decreasing the ion exchange ability of the mixed bed of ion exchange resins.

Therefore, one aspect of the invention relates to a method for removing ionic contaminants from a hydrolysable organic solvent that comprises contacting the hydrolysable organic solvent with a mixed bed of ion exchange resin comprising cationic ion exchange resins and anionic ion exchange resins, wherein the anionic ion exchange resins are selected from weak-base anionic ion exchange resins. Preferably, the weak-base anionic ion exchange resins have tertiary amine groups.

Another aspect of the invention relates to a compound having an ester bond obtained by any of the methods described herein, wherein the concentration of Na, K, Ca, Al, Fe, Ni, Zn, Cu, Cr and Sn are 0.1 ppb or less respectively.

In another aspect, the invention relates to a method for removing ionic contaminants from a hydrolysable organic solvent that comprises the steps of (a) preparing a mixed bed of ion exchange resin comprising cationic ion exchange resins and anionic ion exchange resins, wherein the anionic ion exchange resins are weak-base anionic ion exchange resins, and (b) contacting a hydrolysable organic solvent with the mixed bed of ion exchange resin.

These and other embodiments are described in more detail in the Detailed Description.

DETAILED DESCRIPTION

As used throughout this specification, the abbreviations given below have the following meanings, unless the context clearly indicates otherwise: g=gram(s); mg=milligram(s); L=liter(s); mL=milliliter(s); ppm=parts per million; ppb=parts per billion; m=meter(s); mm=millimeter(s); cm=centimeter(s); min=minute(s); s=second(s); hr.=hour(s); ° C.=degree(s) C.=degree(s) Celsius; vol %=volume percent(s); wt %=weight percent(s).

Methods of the present invention are generally applicable to hydrolysable organic solvents. As used herein, "hydrolysable organic solvent" means a solvent including a compound which may be decomposed to acid and base components by water with or without a catalyst. Hydrolysable organic solvents include but are not limited to esters, amides, carbonates, and mixtures thereof. Examples of esters include propylene glycol methyl ether acetate (PGMEA), ethyl lactate, butyl lactate, ethyl acetate, butyl acetate, diethylene glycol monoethylether acetate, diethylene grycol mono butyl ether acetate, propylene glycol diacetate, ethyl 3-ethoxy propionate and gamma-butylolactone. Examples of amides include N-methylpyrrolidone, dimethyl formamide, dimethyl acetoamide, 3-methoxy-N,N-dimethyl propion amide, N-(2-hydroxyethyl) propion amide and gamma butylo lactam. Examples of carbonates include ethylenecarbonate and propylene carbonate, dimeythyl carnbonate and diethyl carbonate.

Methods of the present invention use a mixed bed of ion exchange resin. A mixed bed of ion exchange resin refers to a mixture of cationic ion exchange resin and anionic ion exchange resin. The cationic ion exchange resin used in the mixed bed of ion exchange resin normally has hydrogen ions as counter cations to neutralize the negative electrical charge of the functional group. The anionic ion exchange resin used in the mixed bed of ion exchange resin is a weak-base anionic ion exchange resin.

As known in this technical area, there are two types of anionic ion exchange resins, i.e. strong-base anionic ion exchange resin and weak-base anionic ion exchange resin. Strong-base anionic ion exchange resin has trimethyl ammonium groups (called Type I) or dimethyl ethanol ammonium groups (Type II) on a surface of a base resin bead. In this specification, those groups are called "strong-base group(s)". Such strong-base groups have a counter anion (e.g. hydroxyl ion ($OH^-$)) to neutralize the positive electrical charge of the group.

The inventors discovered the technical approach of using weak-base anionic exchange resin in a mixed bed of ion exchange resin to purify hydrolysable organic solvent without an undesirable hydrolyzed reaction.

A weak-base anionic ion exchange resin can have primary, secondary or tertiary amine (typically, dimethyl amine) groups on a surface of a base resin bead. As used herein, such groups are called "weak-base group(s)". When a solvent to be purified is contacted with the cationic ion exchange resin, hydrogen ion is released as usual, and released hydrogen ion associates with unshared electron pairs of the nitrogen atom within the weak-base group. Then an anionic impurity is bonded to the weak-base group due to the charge neutral requirement. Consequently, undesired components such as water are not generated by this purification process.

The mixed bed of ion exchange resin also comprises cationic ion exchange resin. Both strong cationic ion exchange resin and weak cationic ion exchange resin can be used for the mixed bed of ion exchange resin in various embodiments of the invention. Strong cationic ion exchange resin includes a cationic ion exchange resin with strong-acid (e.g., sulfonic acid) groups. Weak cationic ion exchange resin includes a cationic ion exchange resin with weak-acid carboxylic acid groups, weak-acid phosphonic acid groups and/or weak-acid phenolic groups.

The ratio of cationic ion exchange resin to anionic ion exchange resin in the mixed bed of ion exchange resin is generally from 1:9 to 9:1 in equivalent ratio of ion exchange groups in some embodiments. Preferably, the ratio is from 2:8 to 8:2.

Sometimes cationic ion exchange resins and/or anionic ion exchange resins contain metal impurities originating from its manufacturing process. Such metal impurities might come out from the resins and cause metal ion contamination in the processed solvent. Without wishing to be bound to any particular theory, the inventors believe that such metal impurities combine with low-molecular weight organic compounds which are contained in the ion exchange resins as a side-reaction product or unreacted product of resins. Such a metal-organic compound complex is more easily dissolved in an organic solvent such that the organic compound carries the metal impurity into an organic solvent. Therefore, the inventors believe that it is desirable to minimize the amount of metal impurities and/or leachable species of low molecular weight organic compounds in the ion exchange resins to decrease the potential for ion contamination in the solvent to be processed.

Metal impurities contained in ion exchange resins can include Na, K, Ca, Al, Fe, Ni, Zn, Cu, Sn and Cr. To prevent metal ion contamination from ion exchange resins, the contents of these metal impurities in ion exchange resins to be used in some embodiments of the present invention are preferably 5 ppm or less respectively, based on the dry-weight of the ion exchange resins. More preferably, the contents of these metal ions are 3 ppm or less based on the dry-weight of the ion exchange resins. The contents of the metals can be analyzed with ICP-MS after resin sample ashing (i.e. burning the ion exchange resins, dissolving the remained ash to hydrochloric acid aqueous solution, and then analyzing the concentrations of metal ions by ICP-MS).

The content of leachable species of low-molecular organic compounds included in ion exchange resins can be evaluated by the following method. Firstly, ultra pure water is flown continuously into an ion exchange resin column at 50 BV/Hr, then TOC (total organic carbon) values of inlet ultra pure water and outlet ultra pure water are measured after two hours flow. Then, the difference, or delta ($\Delta$) TOC value, is calculated from the two TOC values. $\Delta$ TOC value is calculated by subtraction of the inlet TOC value from the outlet TOC value. In some embodiments of the present invention, the $\Delta$ TOC value measured by the above method is preferably 10 ppb or less. More preferably, the $\Delta$ TOC value is 5 ppb or less. TOC can be analyzed by commercially available TOC analysers using techniques known to those of skill in the art.

The cationic ion exchange resin and anionic ion exchange resin originally contain water (swelled by water in equilibrium condition with water). In some embodiments of the present invention, contents of water in the cationic ion exchange resin and anionic ion exchange resin are decreased to 5 wt % or less respectively (i.e., for each resin) prior to use. More preferably, the contents of water in cationic ion exchange resin and anionic ion exchange resin are 3 wt % or less in each resin. To decrease the content of water, cationic ion exchange resin and anionic ion exchange resin can be dried before contacting with a hydrolysable organic solvent. An apparatus of drying and conditions such as temperature, time and pressure for drying ion exchange resins can be selected using techniques known to those of skill in the art. For example, the ion exchange resins can be heated in an oven at 60 to 120° C. for 1 to 48 hours under decompressed condition. The content of water can be calculated by comparison of the weights of ion exchange resin before and after heating it at 105° C. for 15 hours.

When contacting a hydrolysable organic solvent with a mixed bed of ion exchange resin, any known methods for contacting liquids with ion exchange resins can be used. For example, a mixed bed of ion exchange resin can be packed in a column and the solvent can be poured from the top of the column through the mixed bed of ion exchange resin. The flow rate of the solvent can be from 1 to 100 BV/hr, preferably from 1 to 50 BV/hr. As used herein, "BV" means bed volume, and refers to an amount of liquid contacted with the same amount of a hydrated wet mixed bed of ion exchange resin. For example, if 120 ml of a hydrated wet mixed bed of ion exchange resin is used, 1 BV means 120 ml of hydrolysable organic solvent is contacted with the mixed bed of ion exchange resin. 'BV/hr' was calculated by flow rate (mL/hr) divided by bed volume (mL).

The temperature during contacting a hydrolysable organic solvent with a mixed bed of ion exchange resin can be from 0 to 100° C., preferably from 10 to 60° C., more preferably from 20 to 40° C., in various embodiments.

The obtained hydrolysable organic solvent includes quite low-level of metallic and non-metallic ionic contaminations. The contaminations can include Na, K, Ca, Al, Fe, Ni, Zn, Cu, Sn and Cr. The concentrations of these contaminations can be 0.1 ppb or less respectively, in various embodiments. Therefore, hydrolysable organic solvents obtained using methods of the present invention can be useful in applications which requires a quite high level of pure solvent, such as for the manufacture of pharmaceuticals and electronic materials, and especially for use in semiconductor fabrication processes.

Some embodiments of the invention will now be described in detail in the following Examples.

EXAMPLES

Comparative Example 1

Mix bed of Strong Cation Exchange Resin DOWEX™ MONOSPHERE™ 650C UPW(H) and Strong Anion Exchange Resin AMBERJET™ UP4000.

Hydrated wet cation resin MS650 C UPW and hydrated wet anion resin UP4000 are mixed at the weight ratio of 39:61 as 1:1 for stoichiometric ratio. 120 mL of the mix resin is loaded into a Teflon column. Since DOWANOL™ PMA solvent (propylene glycol monomethyl ether acetate, PGMEA) is not compatible with water, DOWANOL™ PM solvent (propylene glycol monomethyl ether, PGME) rinse is done first for 3 days (flow for 6 hr/day at 15 mL/min, flow stopped for nights) to displace water with PGME and to remove organic leachables. It is confirmed that resin shrinkage was stopped and the Bed Volume became stable at 113 mL. Then DOWANOL™ PMA solvent is flowed at 15 mL/min for 8 hr followed by flow stop for a night to displace DOWANOL™ PM solvent with DOWANOL™ PMA solvent. The resin Bed Volume became stable at 89 mL. Then, sampling is done with various flow rates (12 BV/hr, 6 BV/hr and 1.5 BV/hr).

Comparative Example 2

Weak Cation Exchange Resin DOWEX™ MAC-3

One hundred and twenty (120) mL (88 g) of wet weak cation resin MAC-3 is charged to a Teflon column. First, DOWANOL™ PM solvent rinse is done for one day (6 hr flow at 32 mL/min). It was found that resin volume was expanded to 150 mL. Then DOWANOL™ PMA solvent is flowed for 2 hr at 32 mL/min and the flow is stopped for a night. DOWANOL™ PMA solvent flow is resumed in the next day at 16 mL/min and is kept for 7 hr. It is confirmed that resin volume shinkage was stopped at 100 mL. Then the flow is stopped for a night. In the next days, DOWANOL™ PMA solvent flow is resumed and samples are taken at various flow rates (16 BV/hr and 4 BV/hr).

Inventive Example 1

Mix Bed of Weak Cationic Exchange Resin DOWEX™ MAC-3 and Weak Anion Exchange Resin AMBERITE™ IRA98

Sixty (60) mL (46.5 g) of hydrated wet DOWEX™ MAC-3 and 60 mL (41.0 g) of hydrated wet AMBER-LITE™ IRA98 are mixed homogeneously. The equivalent weight based mix ratio is 1:0.28. The mix resin is placed in a vacuum oven at 105-110° C., 40 mmHg for 15 hr to prepare dry resin. Residual water content is confirmed below 1 wt %. The dry resin is charged into a Teflon column. DOWANOL™ PMA solvent is flowed at 8 mL/min for 8 hr. The flow is stopped for a night, and then is resumed. The resin volume in PMA solvatd state is 150 mL. Samples are taken at various flow rates (18 BV/hr, 9 BV/hr and 5 BV/hr).

Inventive Example 2

Mix Bed of Strong Cationic Exchange Resin AMBERJET™ 1024UP H and Weak Anion Exchange Resin AMBERITE™ IRA98

The same procedure as of Inventive Example 1 is conducted excepting for cationic resin is changed to 40 mL of hydrated wet AMBERJET™ 1024 UP H and the amount of AMBERLITE™ IRA98 is changed to 80 mL. The equivalent weight based mix ratio is 1:1. Residual water content is confirmed below 1 wt %. The contents of metals (Na, K, Ca, Al, Fe, Ni, Zn, Cu, Cr and Sn) are under 5 ppm based on the dry-weight of the mixed bed of ion exchange resins. Δ TOC was below 5 ppb. The resin bed volume is PMA solvated state was 96 mL.

Analysys

The concentrations of metals in the samples are analyzed by ICP-MS (Inductively Coupled Plasma-mass spectrometry), and the analytical results are shown in Tables 1 and 2. Original metal level (concentration) and metal element ratio are varied by feed solvent lot. It is considered that the difficulty of removal may be impacted by metal element.

Metal reduction capability is low in Comparative Examples 1 and 2 where more than 50% of metals remained in the treated solvent. Some metals are hardly removed at all. Conversely, in Inventive Examples 1 and 2, metal residuals are less than 20% as the sum of 10 metals.

The hydrolysis decomposition of PGMEA was evaluated with GC-FID (Gas chromatography—flame ionization detector) and the results are shown in Table 3. In Table 3, 'purity' is the percentage of PGMEA including isomer, i.e. the sum of 1-methoxy-2 propyl acetate and 2-methoxy-1-prolyl acetate. PGMEA is decomposed to PGME and acetic acid thorough hydrolysis, as the results PGME and acetic acid are increased, and purity (percentage of PGMEA) is decreased. In GC-FID analysis, PGME increase and purity decrease are monitored. Comparative Examples 1 and 2 show an increase of PGME and a decrease of purity. Covnersely, Inventive Examples 1 and 2 did not show any change in GC results.

TABLE 1

| | Evaluation results of Metal removal capability (Comparative Examples) | | | | | | |
|---|---|---|---|---|---|---|---|
| | Comparative Example 1 | | | Comparative Example 2 | | | |
| Resin type | Mixture of Strong cation exchange/ Strong anion exchange | | | Weak cation resin | | | |
| Ion Exchange resin | MS650C UPW/UP4000 | | | MAC-3 | | | |
| Pretreatment | As received | | | As received | | | |
| Sampling point | Inlet | Outlet | Outlet | Outlet | Inlet | Outlet | Outlet |
| Flow rate (BV/hr) | NA | 12 | 6 | 1.5 | NA | 16 | 4 |
| Concentration of  Na | 0.02 | 0.01 | 0.01 | 0.01 | 0.03 | 0.04 | 0.04 |
| metals (ppb)  Fe | 0.06 | 0.02 | 0.02 | 0.02 | 0.10 | 0.07 | 0.05 |

TABLE 1-continued

Evaluation results of Metal removal capability (Comparative Examples)

|  |  | Comparative Example 1 | | | | Comparative Example 2 | | |
|---|---|---|---|---|---|---|---|---|
| | K | 0.10 | 0.10 | 0.10 | 0.09 | 0.16 | 0.16 | 0.18 |
| | Ca | 0.01 | 0.01 | 0.01 | 0.01 | 0.02 | 0.01 | 0.01 |
| | Cu | 0.03 | 0.03 | 0.02 | 0.02 | 0.09 | 0.08 | 0.08 |
| | Al | 0.14 | 0.15 | 0.14 | 0.14 | 0.09 | 0.11 | 0.09 |
| | Cr | 0.04 | 0.01 | 0.01 | 0.01 | 0.05 | 0.04 | 0.03 |
| | Ni | 0.02 | 0.01 | 0.01 | 0.01 | 0.01 | 0.01 | 0.01 |
| | Zn | 0.42 | 0.09 | 0.09 | 0.11 | 0.35 | 0.25 | 0.22 |
| | Sn | 0.70 | 0.51 | 0.49 | 0.48 | 0.12 | 0.11 | 0.10 |
| SUM of 10 metals (ppb) | | 1.54 | 0.94 | 0.90 | 0.91 | 1.02 | 0.89 | 0.81 |
| Residual of metals (%) | | — | 61 | 58 | 59 | — | 88 | 80 |

TABLE 2

Evaluation results of Metal removal capability (Inventive Examples)

| | | Inventive Example 1 | | | | Inventive Example 2 | | | |
|---|---|---|---|---|---|---|---|---|---|
| Resin type | | Dry mixture of Weak cation exchange resin/Weak anion exchange resin | | | | Dry mixture of Strong cation exchange resin/Weak anion exchange resin | | | |
| Ion Exchange resin | | DOWEX ™ MAC3/AMBERLITE ™ IRA98 Dry mix | | | | AJ1024UPH/IRA98 Dry mix | | | |
| Pretreatment | | Dried | | | | Dried | | | |
| Sampling point | | Inlet | Outlet | Outlet | Outlet | Inlet | Outlet | Outlet | Outlet |
| Flow rate (BV/hr) | | NA | 18 | 9 | 5 | NA | 32 | 16 | 8 | 4 |
| Concentration | Na | 0.02 | 0.00 | 0.00 | 0.00 | 0.12 | 0.02 | 0.01 | 0.01 | 0.01 |
| of metals (ppb) | Fe | 0.44 | 0.02 | 0.02 | 0.04 | 0.10 | 0.01 | 0.01 | 0.01 | 0.02 |
| | K | 0.00 | 0.00 | 0.00 | 0.00 | 0.02 | 0.01 | 0.01 | 0.00 | 0.02 |
| | Ca | 0.02 | 0.00 | 0.00 | 0.00 | 0.01 | 0.01 | 0.01 | 0.00 | 0.01 |
| | Cu | 0.04 | 0.04 | 0.03 | 0.03 | 0.07 | 0.00 | 0.00 | 0.00 | 0.01 |
| | Al | 0.00 | 0.01 | 0.00 | 0.00 | 0.01 | 0.00 | 0.00 | 0.00 | 0.00 |
| | Cr | 0.03 | 0.00 | 0.00 | 0.00 | 0.01 | 0.01 | 0.00 | 0.00 | 0.00 |
| | Ni | 0.02 | 0.00 | 0.00 | 0.00 | 0.00 | 0.00 | 0.00 | 0.00 | 0.00 |
| | Zn | 0.78 | 0.04 | 0.00 | 0.01 | 0.39 | 0.08 | 0.08 | 0.09 | 0.09 |
| | Sn | 0.02 | 0.00 | 0.01 | 0.00 | 0.61 | 0.08 | 0.09 | 0.07 | 0.08 |
| SUM of 10 metals (ppb) | | 1.38 | 0.12 | 0.08 | 0.10 | 1.34 | 0.22 | 0.21 | 0.20 | 0.23 |
| Residual of metals (%) | | — | 9 | 6 | 7 | — | 17 | 16 | 15 | 17 |

TABLE 3

Evaluation of hydrolysis decomposition

| | | | Flow rate (BV/hr) | PGME(area %) | Purity (area %) |
|---|---|---|---|---|---|
| Comparative Example 1 | MS650C UPW/ UP4000 | Original | NA | 0.00 | 99.99 |
| | | Outlet | 12 BV/hr | 0.03 | 99.97 |
| | | | 6 BV/hr | 0.05 | 99.94 |
| | | | 1.5 BV/hr | 0.16 | 99.85 |
| Comparative Example 2 | MAC-3 | Original | NA | 0.00 | 99.99 |
| | | Outlet | 16 BV/hr | 0.01 | 99.99 |
| | | | 4 BV/hr | 0.02 | 99.97 |
| Inventive Example 1 | MAC-3/IRA98 | Original | NA | 0.00 | 99.99 |
| | | Outlet | 16 BV/hr | 0.00 | 99.99 |
| | | | 8 BV/hr | 0.00 | 99.99 |
| | | | 2 BV/hr | 0.00 | 99.99 |
| Inventive Example 2 | AJ1024 UP H/ IRA98 | Original | NA | 0.02 | 99.95 |
| | | Outlet | 32 VB/hr | 0.02 | 99.95 |
| | | | 16 BV/hr | 0.02 | 99.95 |
| | | | 8 BV/hr | 0.02 | 99.95 |
| | | | 4 BV/hr | 0.02 | 99.95 |

The invention claimed is:

1. A method for removing ionic contaminants from a hydrolysable organic solvent selected from the group consisting of an ester, an amide, a carbonate, and mixtures thereof, the method comprising contacting the hydrolysable organic solvent with a mixed bed of ion exchange resin comprising cationic ion exchange resins and anionic ion exchange resins, wherein the anionic ion exchange resins are selected from weak-base anionic ion exchange resins, wherein the contents of Na, K, Ca, Al, Fe, Ni, Zn, Cu, Cr and Sn in the cationic ion exchange resins and the anionic ion exchange resins are 5 ppm or less based on the dry-weight of the cationic ion exchange resins and anionic ion exchange resins, and wherein following contact with the mixed bed of ion exchange resin, the hydrolysable organic solvent comprises 0.1 ppb or less of each of Na, K, Ca, Al, Fe, Ni, Zn, Cu, Sn and Cr.

2. The method of claim 1, wherein the weak-base anionic ion exchange resins have tertiary amine groups.

3. The method of claim 1, wherein the content of water in the cationic ion exchange resins and the anionic ion exchange resins are 5 weight % or less respectively.

4. The method of claim 1, the mixed bed of ion exchange resin comprises 10 ppb or less of leachable species of low-molecular organic compound measured by the following method:

washing the ion exchange resin by 50 BV/Hr of ultra pure water flow for 2 hours, analyzing total organic carbon values of water before and after contacting with the washed ion exchange resin, then calculating the difference of the total organic carbon values of the water by subtracting the total organic carbon value of water after contacting with the ion exchange resin from the total organic carbon value of water before contacting with the ion exchange resin.

5. The method of claim 1, wherein the hydrolysable organic solvent is a compound having an ester bond.

* * * * *